United States Patent
Green et al.

(10) Patent No.: US 8,969,548 B2
(45) Date of Patent: *Mar. 3, 2015

(54) ANTIOXIDANT SMALL MOLECULES AIMED AT TARGETING METAL-BASED OXIDATIVE STRESS IN NEURODEGENERATIVE DISORDERS

(71) Applicant: Texas Christian University, Fort Worth, TX (US)

(72) Inventors: Kayla Nalynn Green, Fort Worth, TX (US); Kimberly Marie Lincoln, Fort Worth, TX (US); Paulina Gonzalez, Fort Worth, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/105,435

(22) Filed: Dec. 13, 2013

(65) Prior Publication Data

US 2014/0206861 A1    Jul. 24, 2014

Related U.S. Application Data (60) Provisional application No. 61/754,012, filed on Jan. 18, 2013.

(51) Int. Cl.
  *C07D 487/00*    (2006.01)
  *A61K 31/4353*    (2006.01)

(52) U.S. Cl.
  CPC .................................. *A61K 31/4353* (2013.01)
  USPC ........................................................ 540/471

(58) Field of Classification Search
  CPC ........... A61K 31/4375; A61K 31/4353; C07D 47/048
  See application file for complete search history.

(56) References Cited

U.S. PATENT DOCUMENTS

2004/0204344 A1    10/2004 Huang
2011/0110850 A1    5/2011 Barnham et al.

OTHER PUBLICATIONS

Richardson, T., et al. "An N-Heterocyclic Amine Chelate Capable of Antioxidant Capacity and Amyloid Disaggregation." ACS Chem Neurosci. (2012), vol. 3, pp. 919-927.*
Costa, J., et al. "Metal Complexes of Macrocyclic Ligands Containing Pyridine." Inorg. Chem. (1993), vol. 32, pp. 5257-5265.*
Lincoln, K.M., et al. "A potent antioxidant small molecule aimed at targeting metal-based oxidative stress in neurodegenerative disorders." Chem. Comm. (2013), vol. 49, pp. 2712-2714.*
Paul A. Adlard, et al.; "Metal Ionophore Treatment Restores Dendritic Spine Density and Synaptic Protein Levels in a Mouse Model of Alzheimer's Disease"; article; 7 pages; Mar. 2011, vol. 6, Issue 3, e17669 PLoS ONE; www.plosone.org.
Noel G. Faux, et al.; "PBT2 Rapidly Improves Cognition in Alzheimer's Disease: Additional Phase II Anaylses"; Journal of Alzheimer's Disease; 9 pages; IOS Press; copyright 2010.
Peter E. Crouch, et al.; "The Alzheimers Therapeutic PBT2 Promotes Amyloid-β Degradation and GSK3 Phosphorylation Via a Metal Chaperone Activity"; Article; Journal of Neurochemistry; 11 pages; copyright 2011; International Society for Neurochemistry.
Alaina S. Detoma, et al.; "Myricentin: A Naturally Occurring Regulator of Metal-Induced Amyloid-β Aggregation and Neurotoxicity"; ChemBioChem; 4 pages; copyright 2011; Wiley-VCH Verlag GmbH & Co. KGaA, Weinheim.
Lincoln, et al., An Antioxidant Chelate in Response to Metal-Induced Amyloid Aggregation in Alzheimer's Disease (2013); http://www.srs.tcu.edu/previous_posters/Chemistry/2012/277-Lincoln-Green.pdf.

* cited by examiner

*Primary Examiner* — Noble Jarrell
*Assistant Examiner* — John S Kenyon
(74) *Attorney, Agent, or Firm* — Charles D. Gunter, Jr.

(57) ABSTRACT

Amine chelates capable of antioxidant capacity and amyloid disaggregation are shown which may be useful in targeting metal-based oxidative stress in neurodegenerative disorders. Pyclen, a backbone commonly investigated for contrast agent imaging, may be repurposed as an anti-oxidant chelator for disaggregating amyloid. The antioxidant capacity of pyclen was enhanced dramatically via conversion of the pyridine backbone to a pyridol with cellular studies showing superior antioxidant capacity while retaining chelation ability to protect amyloid from metal ions aggregation and also disaggregate amyloid aggregates.

1 Claim, 7 Drawing Sheets

Figure 1. Turbidity Assay showing disaggregation of amyloid plaques upon incubation (24 hours at 37 °C) with 1-4. Solutions prepared in 15 mM $KH_2PO_4$/NaCl buffer. [$A\beta_{1-40}$] = 200 µM, [$CuSO_4$] or $Zn(OAc)_2$ = 400 µM, [chelator] = 800 µM. n=3 for each sample. When SEM are not depicted, they were too small to graph.

Figure 2. The addition of ligands 1 - 4 to aggregated $A\beta$ results in reconstitution of $Tyr^{10}$ fluorescence which was decreased due to aggregate formation. Solutions prepared in 15 mM $KH_2PO_4$/NaCl buffer. [$A\beta_{1-40}$] = 200 µM, [$CuSO_4$] or [$Zn(OAc)_2$] = 400 µM, [chelator] = 800 µM. n=3 for each sample.

Figure 3. TEM Images showing (a) copper induced aggregation of amyloid and (b) its dissolution by 1.

Figure 4. Fluorescence intensity of 7-hydroxy-CCA after incubation of CCA [100uM] and ascorbate [300uM] with $Cu^{II}$(■)[40uM]. Compound 1(◊) and 3(X) [40uM] were added at t=0 s prior to $Cu^{II}$. Asc(▲) is a negative control with buffer and ascorbate only. All solutions, except $Cu(NO_3)_2$ (milli-Q water only) were dissolved and diluted in KH2PO4/NaCl [15 mM] buffer containing desferryl [2 μM]. Final volume = 4 mL, n = 3 for each sample.

Figure 5. Calcien AM viability assay of FRDA cells after 48 hour exposure to BSO [1 mM] with 1-4 [1 nM final]. n=4 for each sample. * Indicates significance with a p value < 0.05.

Figure 6. DCFH-DA fluorescent response in FRDA cells after 12 hours exposure to BSO [1 mM] with 1-4 [4 nM]. n=4 for each sample. * Indicates significance with a p value < 0.05.

Figure 7. DCFH-DA fluorescent response in FRDA cells after 12 hours exposure to BSO [1 mM] showing dose dependence with 1. n=4 for each sample. * Indicates significance with a p value < 0.05.

Figure 8. DCFH-DA fluorescent response to chelator 1 in HT-22 cell line. Growth media serves as the positive control and is normalized to 100% while glutamate serves as the negative control. ZYC26 was 1 µM and serves as a positive control for antioxidant ability. *** indicates significance with a p value < 0.001.

Figure 9. DCFH-DA fluorescent response in FRDA cells after 12 hours exposure to BSO [1 mM] showing dose dependence with 1 and 2. n=8 for each sample. *Indicates significance with respect to BSO control and a p value < 0.05.

Figure 10. Calcein AM viability assay of FRDA cells after 48 hour exposure to BSO [1 mM] followed by addition of 2 [various concentrations]. n=8 for each sample. *Indicates significance with respect to BSO control and a p value < 0.05.

Figure 11. Fluorescence response of FRDA cells incubated with Calcein AM viability indicator (a) FRDA cells in media only (b) + BSO [1 mM] (c) b + 12.5 nM 2 (d) b + 125 nM 2 (e) b + 1.25 uM 2 (f) b + 12.5 uM 2.

Figure 12. Turbidity Assay showing (a) preventative and (b) disaggregative capability of 2 compared to 1, cyclen and EDTA to prevent amyloid plaques. [A$\beta_{1-40}$] = 200 nM, [CuSO$_4$] or Zn(OAc)$_2$ = 400 nM, [chelator] = 800 nM with 15mM KH$_2$PO$_4$/NaCl buffer. n=3 for each sample.

Figure 13. SEM Images showing the prevention of amyloid. a) Aβ (b) Aβ + Cu$^{II}$ (c) b+1 (d) b+2 (e) b + cyclen (f) b+ EDTA.

ANTIOXIDANT SMALL MOLECULES AIMED AT TARGETING METAL-BASED OXIDATIVE STRESS IN NEURODEGENERATIVE DISORDERS

CROSS REFERENCE TO RELATED APPLICATIONS

The present application claims priority from a provisional application Ser. No. 61/754,012, filed Jan. 18, 2013, entitled "Antioxidant Small Molecules Aimed At Targeting Metal-Based Oxidative Stress In Neurodegenerative Disorders", by the same inventors.

BACKGROUND OF THE INVENTION

1. Field of the Invention

The present invention relates the development of potent biomodal antioxidant small molecules capable of beta-amyloid prevention and disaggregation and for targeting metal-based oxidative stress in neurodegenerative disorders.

2. Description of the Prior Art

Alzheimer's disease (AD) is a debilitating disease that affects over 5.4 million people currently, at an annual cost exceeding 180 billion dollars in the U.S. alone. Physiological and molecular features include the deposition of beta-amyloid (Aβ) plaques, elevated levels of transition metals and oxidative stress. The exact mechanism leading to AD is still not-established, although amyloid is a component in many hypotheses proposed to date. Recent attention has implicated metal ions in the cascade leading to the physiological and pathological hallmarks of AD thus forming the "Metal Hypothesis of Alzheimer's Disease".

Transition metals are trace elements vital for normal biological function because they serve as structural drivers, cofactors or reactive centers in proteins and enzymes. Fenton chemistry is defined by the oxidation of redox active metal ions in their reduced from, such as $Fe(II)$ or $Cu(I)$, with $H_2O_2$ to produce radicals that are known to cause DNA oxidation, disruption of mitochondrial membrane potentials, lipid peroxidation. Redox chemistry of these elements is tightly regulated throughout biology via regulatory and chaperone systems, so that protein modification, in conjunction with Fenton chemical reactions, producing cellular oxidative stress will be avoided. Disruptions or alterations in the redox potential of metal-ion regulatory systems have therefore been implicated in a number of disease states to date which include: Huntington's, Alzheimer's, and Parkinson's, Lou Gehrig's disease, as well as macular degeneration and Freidrich's ataxia. For example, a histidine rich binding site has been identified in $Aβ_{1-40}$ or $Aβ_{1-42}$. Insoluble beta-amyloid plaques (Aβ) have increased levels of copper, zinc and iron, while intracellular copper stores are deficient in AD patients. Metal ion chelation by amyloid plaques gives rise to concomitant free radical generation, resulting in neuronal death. Furthermore, increased levels of oxidative stress have been, in-part, attributed to alterations in the expression of superoxide dismutase, as well as protein metal-ion chaperones. Modifications in the levels of metal-ion chaperone expression associated with the signal transduction pathway of glutamate receptors, for example, have also been noted with concomitantly higher levels of cleaved amyloid precursor protein to produce $Aβ_{1-40}$ or $Aβ_{1-42}$. Finally, aged populations naturally exhibit increased levels of ROS due to decreased levels of antioxidants such as melatonin, resulting in higher levels of oxidative stress. However, AD models suggest more exacerbated levels of ROS, thus resulting in AD progression.

There is no effective or preventative protocol prescribed for AD, nor have proposed therapies found success in symptom alleviation neurodegenerative decline associated with AD. Many hypothetical pathways of AD have been targeted, one taking aim at the metal-based hypothesis proposed by Bush et al. Synthetic targets focused on inhibiting the interactions of Aβ with metal ions, along with atypical metal ion homeostasis are limited by ion specificity, an inability to cross the blood brain barrier (BBB), and/or biological compatibility. A compound finding exception to these roadblocks has been evaluated in Phase II clinical trials. The chelator clioquinol (CQ) provided improved cognition in mouse models, but its widespread use has been terminated by the adverse side effect of subacute myelo-optic neuropathy. The positive effects exhibited by CQ encourage synthetic chemists to pursue the chelator strategy as a route to potentiating the cognitive decline associated with metal-ion mis-regulation and plaque deposition. A second generation congener of CQ, PBT2, has been produced and is in Phase II clinical trials. Studies of this compound showed improved cognition in AD transgenic mice, and demonstrated positive effects on the learning and memory in AD patients. In contrast to this agent serving as a chelator as utilized in the sense of typical metal-overload disorders, i.e., removing excess metal, the authors have shown that these compounds can serve as neuromodulators by restoring the metal-ion imbalance for neurochemical communication pathways involved in synaptic activity. When the "lost" metal ions that lead to Aβ deposition are rescued by these synthetic chaperones, their activities in the communication pathways are restored, and Aβ clearance is elevated. With these results, the pursuit in biologically compatible transition metal-ion ligands as therapy for AD is encouraged.

SUMMARY OF THE INVENTION

As previously discussed, the misregulation of metal ions is known to produce ROS that lead to neurological degradation associated with Alzheimer's disease in addition to their interaction precipitating amyloid plaques. A molecular system capable of bimodal modulation of the metal-ions in amyloid as well as regulation of the increased levels of ROS would prove useful in combating this disease. To address these issues, we have shown that 1, a backbone previously investigated for contrast agent imaging, may be repurposed as an anti-oxidant chelator for disaggregating amyloid. Compound 1 will be compared to compounds 2-4 in the detailed description of the invention which follows:

Chart 1

|  | pyclen 1 | cyclen 2 | cyclam 3 | EDTA 4 |
|---|---|---|---|---|
| log K constants | | | | |
| $Cu^{II}$ | 20 | 23 | 27 | 9.18 |
| $Zn^{II}$ | 14 | 16 | 15 | 8.41 |

Spectroscopic and TEM/SEM imaging studies show its ability to protect amyloid from copper ions and also disaggregated amyloid aggregates as well. The antioxidant assays show that 1 has antioxidant capacity in vivo and protective capabilities via Calcein AM studies. The DFT studies and direct reactions with $H_2O_2$ show that the pyridine backbone is the key to this ability.

In addition, Applicant's have learned that the antioxidant capacity of 1 can be enhanced dramatically via conversion of the pyridine backbone to a pyridol to produce 2:

Cellular studies show superior antioxidant capacity while retaining chelation ability to protect amyloid from metal ions aggregation and also disaggregate amyloid aggregates. Direct reactions with $H_2O_2$ show that the pyridol backbone is the key to this ability due to the formation of di-keto species of 2.

Additional objects, features and advantages will be apparent in the written description which follows.

DETAILED DESCRIPTION OF THE INVENTION

The embodiments herein and the various features and advantageous details thereof are explained more fully with reference to the non-limiting embodiments that are illustrated in the accompanying Figures and detailed in the following description. The examples used herein are intended merely to facilitate an understanding of ways in which the invention herein may be practiced and to further enable those of skill in the art to practice the invention. Accordingly, the examples should not be construed as limiting the scope of the claimed invention.

Part I:

Utilizing a rational design approach, this work focuses on the use of pyclen (1) shown in Chart 1 as a metal-ion passivation and antioxidant agent based on this ligand's specific metal-ion binding affinity for copper(II) and zinc(II) along with built-in antioxidant functionalities. The ligand is the backbone to PCTA, a potential MRI contrast agent explored in recent years and has been repurposed for Applicant's work.

$H_2O_2$. As Tyr[10] is located within proximity to the metal binding pocket in $A\beta_{1-40}$ the fluorescence intensity of the phenolic side chain decreases during the folding process due to environmental changes that occur locally. This work was supported by circular dichroism spectra, which verified that fluorescence intensity decreased as the conformation of amyloid changed to beta-sheets. Yang and colleagues showed that this spectroscopic marker could be used to follow the folding induced by the addition of copper ions to amyloid, and related the production of $H_2O_2$ to this process. Applicant's hypothesis was that Tyr fluorescence intensity should be restored to Chart 1

| | pyclen 1 | cyclen 2 | cyclam 3 | EDTA 4 |
|---|---|---|---|---|
| | log K constants | | | |
| $Cu^{II}$ | 20 | 23 | 27 | 9.18 |
| $Zn^{II}$ | 14 | 16 | 15 | 8.41 |

Figure 1:
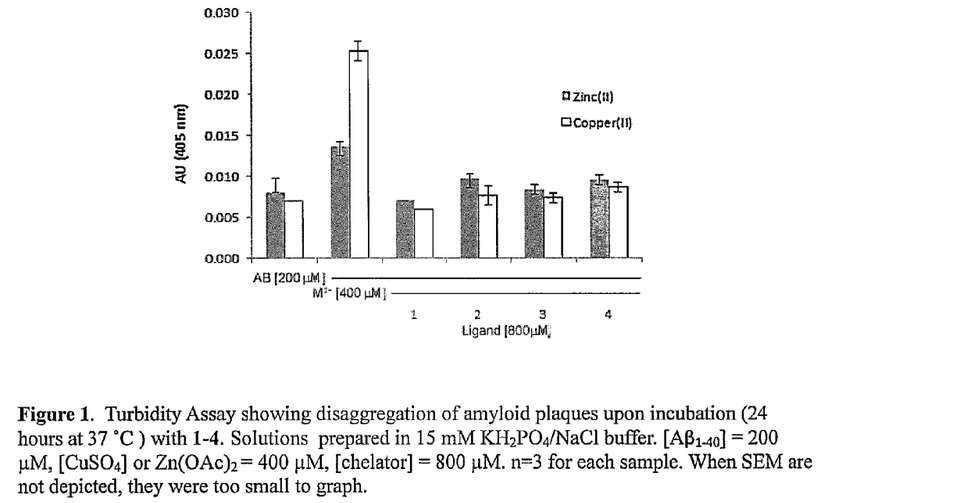
FIG. 1 is a Turbidity Assay graph showing disaggregation of amyloid plaques upon incubation (24 hours at 37° C.) with 1-4 described in the detailed discussion which follows.

Metal ions (copper and zinc) bind to a histidine rich domain in amyloid producing Aβ in the form of insoluble plaques. This process has been comprehensively studied and described in a number of recent reviews. The aggregation of amyloid can be followed by simple spectroscopic techniques such as turbidity and tyrosine fluorescence studies. These methods were used to investigate the ability of 1 to dissociate pre-formed amyloid aggregates upon addition of metal ions, as well as prevent amyloid aggregation. As shown in FIG. 1, copper (II) or zinc (II) ion addition to a solution of $A\beta_{1-40}$ results in a visibly turbid solution which scatters light with a consequential increased absorbance signal, using absorption spectrophotometry. The aggregation observed upon metal ion addition can be reversed by co-incubation of 1 for 4 hours, indicating dissolution of the amyloid aggregates. A visible dissolution of the peptide solution is concomitant to the decrease in absorbance signal. For comparison, this experiment was repeated with 2 and 3 (Chart 1) previously studied by Hindo et. al as Aβ dis-aggregating agents, which Applicant's studies corroborate. The known open-chain chelator EDTA was used as a positive control, and Applicant's studies demonstrated that all ligands were equally successful in disrupting turbidity of the aggregated amyloids. In a similar study, the protective capability of 1 was compared to 2-4. The ligands (1-4) were first co-incubated with amyloid and then metal-ions were added. The ligands displayed an ability to prevent metal-induced aggregation of amyloid upon exposure to copper (II) or zinc (II) salts.

Figure 2:
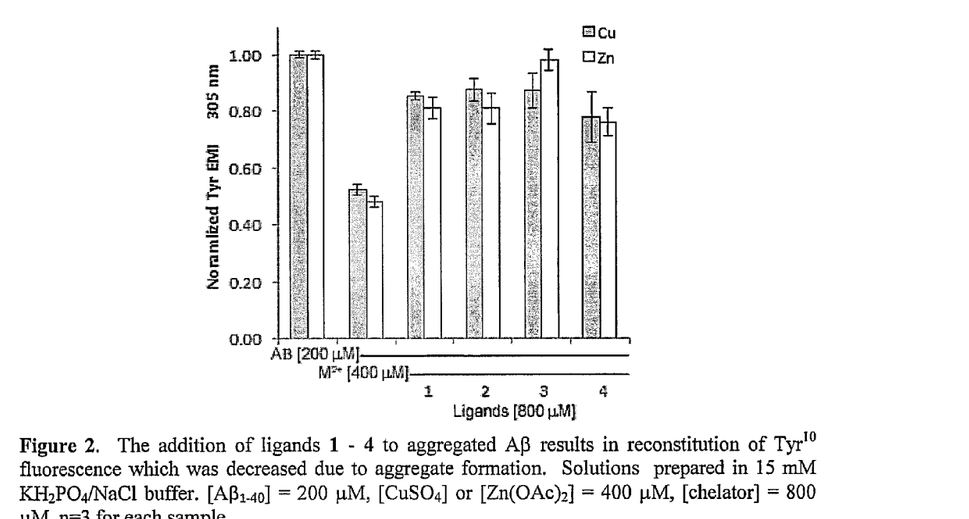
FIG. 2 is a graph showing the addition of ligands 1-4 to aggregated Aβ results in reconstitution of $Tyr^{10}$ fluorescence which was decreased due to aggregate formation.

To further determine the capability of 1 to prevent or disrupt metal-ion induced amyloid aggregation, Applicant's studied Tyr fluorescence intensity. Recent reports have also utilized the natural fluorescence of the native Tyr[10] in the $A\beta_{1-40}$ sequence to study the conformational dynamics of amyloid folding as it relates to AD and/or production of control levels upon addition of 1-4 to a solution of pre-formed metal aggregates, as shown below in FIG. 2. These results are consistent with the turbidity studies presented above. Similar results were also obtained for amyloid samples co-incubated with 1-4 prior to metal ion addition. That is, the ligand chelates show a protective capability by preventing the production of aggregates as evidenced by higher Tyr[10] fluorescence signal compared to the control of amyloid co-incubated with copper(II) or zinc(II), which showed a large decrease in signal intensity after 24 hours.

Figure 3:
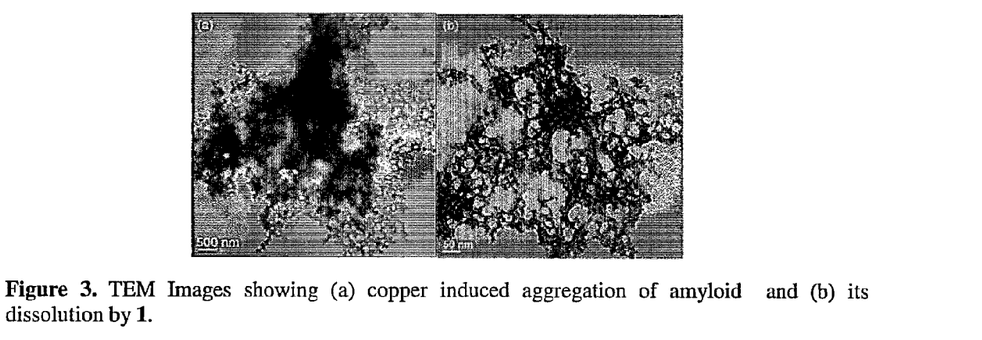
FIG. 3 is an illustration of TEM Images showing (a) copper induced aggregation of amyloid and (b) its dissolution by 1.

Transmission electron microscopy (TEM) and Scanning Electron Microscopy (SEM) were utilized to study the morphology of the aggregates with and without chelators, as well. The TEM images shown in FIG. 3 demonstrate that 1 decreases the amyloid aggregate size by 1-2 orders of magnitude compared to the copper aggregates. Grid (a) shows the large aggregates formed by the addition of metal ions to amyloid (scale 500 nm). Aliquots from the stock used to make grid (a) were then incubated with 1 for 12 hours and then prepared for microscopy. The sizes of the aggregates upon treatment with 1 are an average of 1-2 orders of magnitude smaller and observably more diffuse, as shown in grid (b). SEM images also confirm the ability of the chelates to affect aggregate size as well.

As increased levels of ROS are associated with AD, Applicant's set out to investigate the antioxidant character of 1 compared to the heterocycles 2 and/or 3. Initially, Applicant's showed that 1 was capable of preventing the formation of the ABTS. radical most effectively compared to 2-4 at ligand concentrations of 100 μM. These results were standardized against Trolox (a known antioxidant) with 1 providing 0.4 Trolox equivalents and 2-4 resulting in values of 0.23, 0.11 and 0.15 respectively. Moreover, many of the pathways proposed to produce ROS leading to AD pathology involve metal ions. Applicant's therefore utilized the Cu-ascorbate redox system, Scheme 1, as a model to determine if the ligands could halt copper based redox activity under aerobic conditions:

Scheme 1. Redox cycling of copper in the presence of oxygen and ascorbate to produce OH•.

Figure 4:
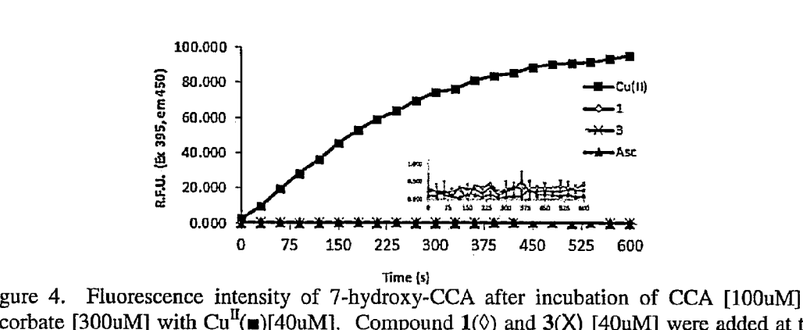
FIG. 4 is a graph showing Fluorescence intensity of 7-hydroxy-CCA after incubation of CCA [100 uM] and ascorbate [300 uM] with $Cu^{II}$(■)[40 uM].

This system is a useful model for studying the brain, as high levels of oxygen and ascorbate are present. Faller and co-workers employed this system to investigate the redox chemistry of amyloid systems with Cu. Coumarin-3-carboxylic acid (CCA), which generates fluorescent 7-hydroxy-CCA in the presence of hydroxyl radicals, was used to quantify the reduction of oxygen by copper redox-cycling in the presence of ascorbate. FIG. 4 shows that copper and ascorbate generate OH. as measured by 7-hydroxy-CCA which increases linearly for the first 5 minutes, and then plateaus around 10 minutes. This process is prevented entirely as shown in the inset of FIG. 4 when 1 or 3 are co-incubated with the Cu-ascorbate system, indicating these ligands are capable of halting copper redox cycling via metal complexation. Next, the ability of 1 to halt hydroxyl generation was compared to $A\beta_{1-40}$, in which Faller reports a decrease the Cu-Ascorbate redox cycle. The Cu-ascorbate system was initially co-incubated with CCA for two minutes showing an increase in fluorescent signal as expected. At this point either 1 or $A\beta_{1-40}$ were added to the Cu-ascorbate system, resulting in a leveling of the 7-hydroxy-CCA signal. This indicated that the addition of 1 or AB1-40 was able to halt the copper redox cycling due chelation of the metal-ion. This redox silencing was verified by the addition of ascorbate to Cu(1) or Cu($AB_{1-40}$) in the presence of CCA resulting in absence of a fluorescent signal during the 10 minute timescale.

Figure 5:
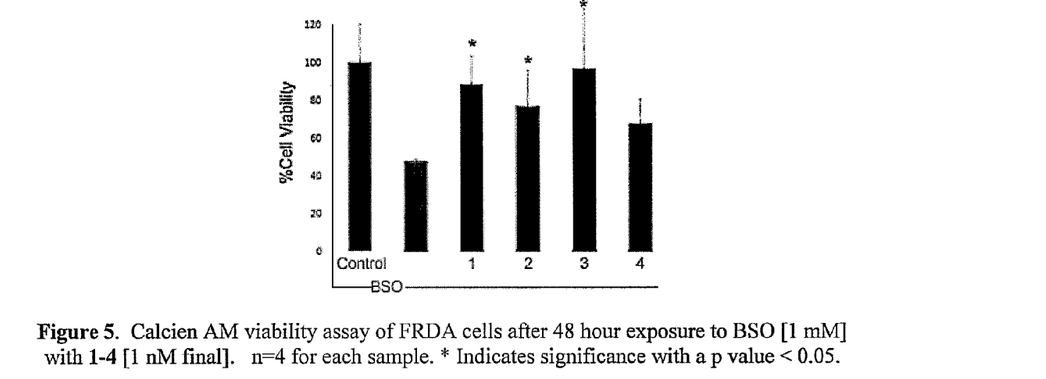
FIG. 5. is a graph showing a Calcien AM viability assay of FRDA cells after 48 hour exposure to BSO [1 mM] with 1-4 [1 nM final].

Cellular studies were then carried out to evaluate the intra-cellular efficacy and toxicity of 1. Preliminary screens compared the cell viability of 1-4 in an FRDA cell line (Fibroblasts from a Friedreich's Ataxia patient) and ability to negate oxidative stress. FRDA cells have higher levels of ROS due to mitochondrial misfunction associated with frataxin expression and therefore serve as a good model for ROS protection. FIG. 5 shows the normalized results of cell (FRDA) viability studies with compounds 1-4 at 1 nM final concentration. Calcein AM, a non-fluorescent, hydrophobic compound that easily permeates intact, live cells, was used as an indicator for cell viability. Calcein AM is hydrolyzed by intracellular esterases producing calcein, a hydrophilic, strongly fluorescent compound that is well-retained in the cell cytoplasm. Compared to the control containing untreated cells, incubation with either 1 or 3 exhibited >85% cell viability at the concentration studied, a statistically significant increase from cells treated with BSO-alone, which had a cell viability of ~45% compared to control cells. Compounds 2 and 4 were less efficatious, but still provide cell viability of greater than 60%. These results confirm that the heterocyclic compounds are compatible for use in cells by providing protection against oxidative stress induced by BSO. Moreover, the addition of the pyridine ring (1) into the heterocyclic core does not induce cell death and, in fact, prevents ROS induced cell death most effectively.

The antioxidant activity of 1 compared to 2-3 was then studied using the cell-permeable fluorophore 2,7'-Dichlorodihydrofluorescin diacetate (DCFH-DA) as an indicator for ROS. DCFH-DA diffuses into cells and is deacetylated by cellular esterases to non-fluorescent 2',7'-Dichlorodihydrofluorescin (DCFH). This species is subsequently oxidized to the highly fluorescent 2',7'-Dichlorodihydrofluorescein (DCF) species in the presence of ROS. The fluorescent intensity is directly proportional to the amount of ROS present in cell cytosol. BSO (2-amino-4-(butylsulfonimidoyl)butanoic acid) was used to inhibit the first step of de novo glutathione synthesis, allowing us to observe the elevated intra-cellular [ROS] are thereby observed.

Figure 6:
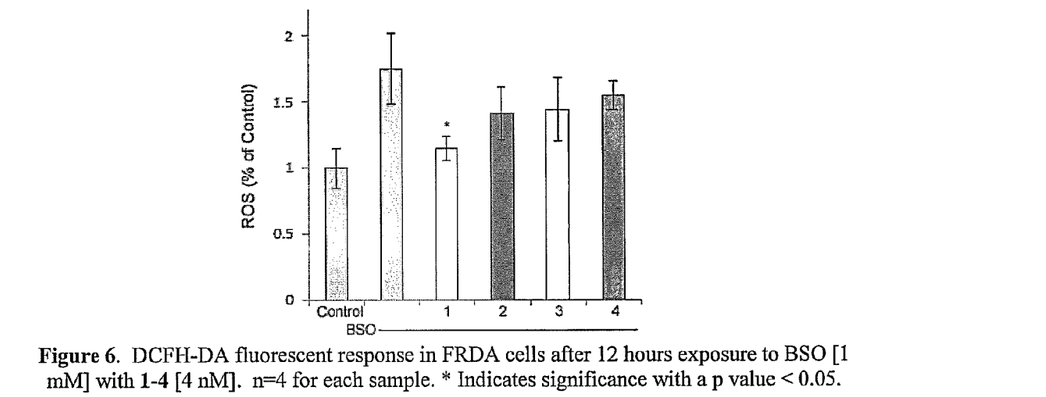
FIG. 6. is a graph showing DCFH-DA fluorescent response in FRDA cells after 12 hours exposure to BSO [1 mM] with 1-4 [4 nM].
Figure 7:
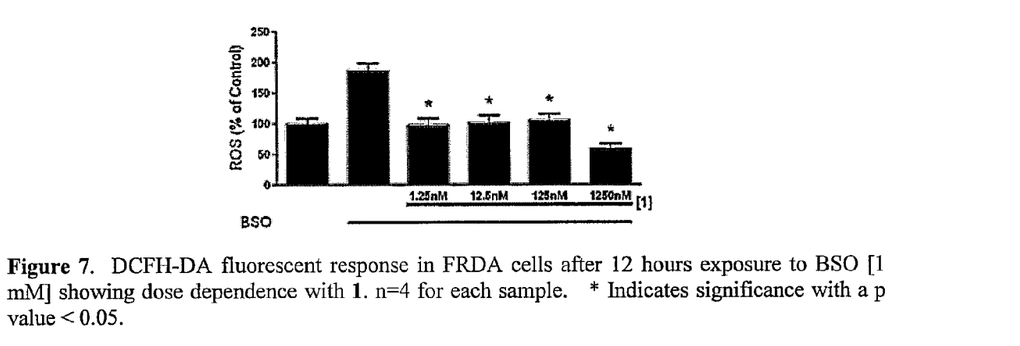
FIG. 7. is a graph of DCFH-DA fluorescent response in FRDA cells after 12 hours exposure to BSO [1 mM] showing dose dependence with 1.
Figure 8:
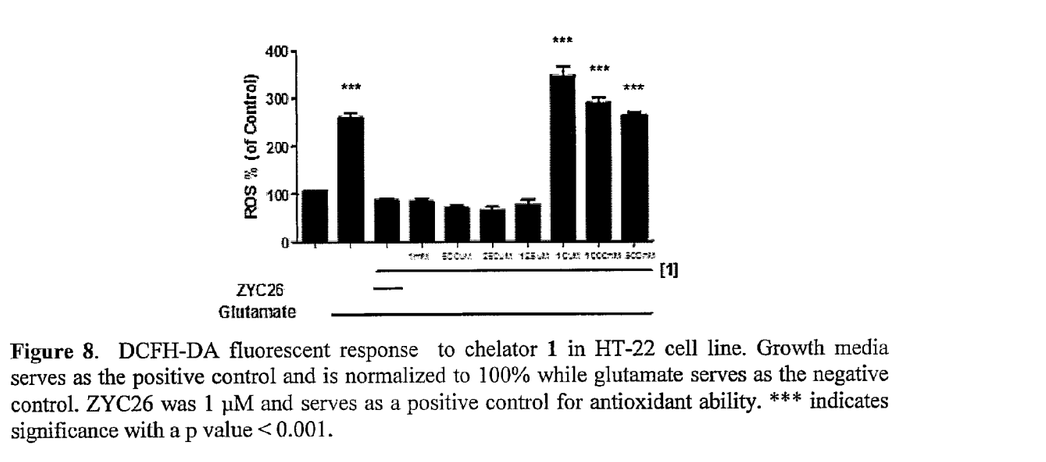
FIG. 8. is a graph of DCFH-DA fluorescent response to chelator 1 in HT-22 cell line.

The results of DCFH-DA cell culture assay shown in FIG. 6 indicate that 1 is the most effective antioxidant at low nM concentrations, significantly attenuating the ROS produced by BSO, with only a 15% increase of ROS over the negative control (media) when compared to 2-4. These results are compared to the positive control BSO-treated cells, with a nearly 1.8 fold increase in ROS. FIG. 7 shows that 1 is an effective antioxidant in the 1.25 nM to 1.25 μM range for the FRDA cell line as well. These results are consistent with results from the Trolox antioxant assay where it was noted that pyclen shows a superior antioxidant activity with and without metal ions present. This was repeated in a neuronal cell line (HT-22) and 1 showed antioxidant nature in the 1 mM-125 uM range (FIG. 8) with a glutamate assault which results in cell death by oxidative glutamate toxicity.

A comparison of these results with the cell viability studies discussed above show that the pyridine ring of 1 is responsible for the antioxidant capacity observed. The heterocyclic compounds 2 and 3 which showed cell viability congruent to 1 with BSO assault (FIG. 4) are structurally similar to 1 except for the pyridine ring. While 1-3 are all largely capable of preventing cell death induced by BSO, ligand 1 is capable of reducing ROS to the greatest extent, thus resulting in the most effective protective capacity. Applicant's attribute this to the pyridine core. It is further postulated that the ability to prevent BSO induced cell death is a result of metal-ion scavenging capacity of these ligands 1-3. An interesting feature to be noted from these cellular studies is the fact that 1 is capable of entering cells and does not appear to interupt the vital functions of cytosolic metalloenzymes via extraction metal ions from those functionalities.

Applicant's have postulated that the observed antioxidant activity of 1 is structurally correlated with the pyridine backbone, as evidenced by the radical studies and incubation of ligands with cells in the DCFH-DA cell culture assays presented above. Schugar and Orvig et al. have each reported antioxidant activity with pyridine like aromatic chelators in separate studies as well. The Weighardt group has computationally and spectroscopically studied bipyridine-based chelates, and their studies prove that the lowest unoccupied molecular orbital (LUMO) of the metal derivatives are composed of mainly ligand π-character.

Applicant's have observed pyclen to be antioxant in the presence of copper ions, this methodology was applied to 1-3 and their $Cu^{II}$ derivatives using DFT (B3LYP, 6-311G (d,p for copper complexes)) to show that the LUMO orbital of 1 and Cu-$1^{2+}$ is largely centered on the pyridine ring. It can be shown that the HOMO of 1 has more electron density on the nitrogen atoms and the LUMO of 1 is composed of >90% π-character as compared to 2 and 3 which have density dispersed throughout. Moreover, the HOMO orbital of 1 is higher in energy compared to 2 as well. The other heterocyclic ligands 2-3 lack these features, i.e. the LUMO being antibonding character alone. Ligands 2 and 3 lack this component and therefore have the LUMO orbital spread throughout the ligand set in an anti-bonding orbital centered on the nitrogen atoms trans to one another, making reactivity less favored.

This is not surprising given that heterocycles containing aromaticity are reported to be highly reactive toward radicals produced via radiolysis of water and naturally react with the heterocycles by addition. Pyridine containing analogs have long been reported in the literature to be potent antioxidants, which is attributed to the electron deficient nature of the pyridine ring, with potency increasing as electron attracting groups are added onto the ring. Such reactivity is well documented, that is pyridine based compounds are known to produce N-oxides upon incubation with $H_2O_2$. To further support this, 2 and 3 lack the pyridine ring but retain the secondary amines in the heterocyclic core and show little potency in the assays presented. The secondary amines, therefore, are less prone to produce N-oxides than the pyridine backbone. Interestingly, 2-3 do show a degree of anti-oxidant capacity which Applicant's postulate to be an effect of the redox tuning of the ligands on the copper ion, rather than ligand composition itself.

Part II:

The foregoing work led to the search for additional molecules having enhanced antioxidant power, compared to the parent 1, while retaining the anti-aggregate capacity. The second part of this work focuses on the use of 2 as a metal-ion passivation and antioxidant agents based on this ligand's specific metal-ion binding affinity and built-in antioxidant functionalities. Oxidative stress is a recurring theme among neurological disorders including AD, Parkinson's and stroke and will therefore serve as the major focus of the work presented herein as the therapeutic target of 2:

Antioxidant Character.

The in situ capacity of 1 to quench free radicals was first explored using the radical ion DPPH (2,2-diphenyl-1-picrylhydrazyl) and indicated that 1 was an effective antioxidant in the entire 37.5-675 mM range screened. Moreover, a preliminary cell-viability screen of 1 showed a large degree of tolerance in two separate cell lines. Given this success the new congener 2 was produced and showed an enhanced ability to reduce free radicals in solution in the same assay. Compound 2 exists largely as the pyridol tautomer as confirmed by NMR.

The reactivity of pyridol/pyridone based compounds such as chelidamic acid have shown reactivity with OH radicals in solution to form bis-pyridones and is a different mechanism than pyridine based compounds such as 1. This reactivity is attributed to the enhanced antioxidant capacity observed. Chelidamic acid is the pyridone congener to the starting material used to produce 1. Therefore similar methodologies to produce 2 in gram scale quantities were employed.

Figure 9:
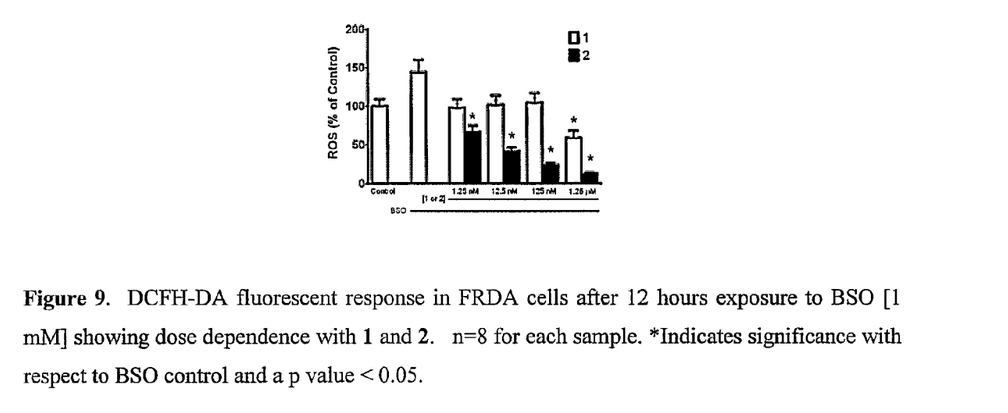
FIG. 9. is a graph of DCFH-DA fluorescent response in FRDA cells after 12 hours exposure to BSO [1 mM] showing dose dependence with 1 and 2.

Cellular studies were carried out to evaluate the intracellular antioxidant efficacy and toxicity of 2 compared to 1 using the cell-permeable fluorophore 2,7'-dichlorodihydrofluorescin diacetate (DCFH-DA) as an indicator for ROS. DCFH-DA diffuses into cells and is deacetylated by cellular esterases to non-fluorescent 2',7'-dichlorodihydrofluorescin (DCFH) which is subsequently oxidized to the highly fluorescent 2',7'-dichlorodihydrofluorescein (DCF) species in the presence of ROS. The fluorescence intensity is directly proportional to the amount of ROS present in cell cytosol.[11] BSO (2-amino-4-(butylsulfonimidoyl)butanoic acid) is a commonly used model for oxidative stress via inhibition of cytosolic glutathione synthesis resulting in elevated intra-cellular [ROS] and an increased fluorescent signal in the presence of DCFH (FIG. 9).

The results of the DCFH-DA cell culture assay indicate that 1 is an effective antioxidant in the 1.25 nM to 1.25 µM range. As shown in FIG. 9 compound 2 is a potent antioxidant at each of the concentrations tested from 1.25 nM to 1.25 µM. While 1 is capable of quenching the ROS induced by BSO, 2 also inhibits the naturally occurring ROS present when compared to the control cells (in growth media only). FIG. 9 shows that at 1.25 nM, 12.5 nM, 125 nM and 1.25 µM [2] there is a decrease of 33%, 58%, 75%, and 87% [ROS] respectively, compared to the untreated cells.

Figure 10:
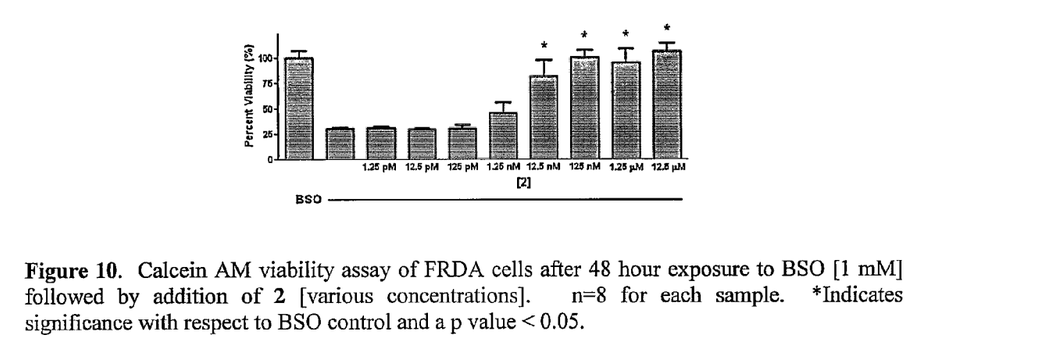
FIG. 10. is a graph showing Calcein AM viability assay of FRDA cells after 48 hour exposure to BSO [1 mM] followed by addition of 2 [various concentrations].
Figure 11:
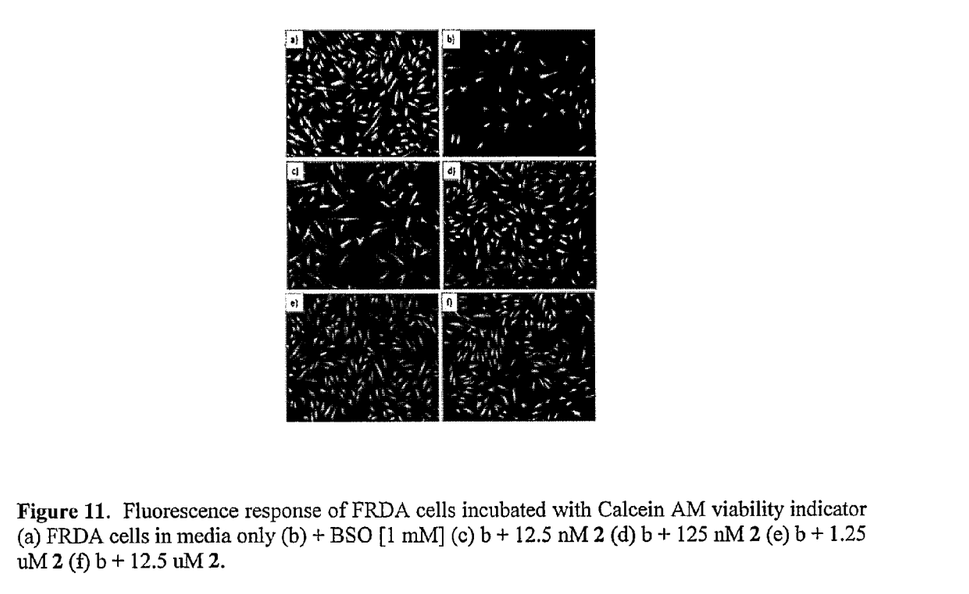
FIG. 11. is an illustration of Fluorescence response of FRDA cells incubated with Calcein AM viability indicator (a) FRDA cells in media only (b)+BSO [1 mM] (c) b+12.5 nM 2 (d) b+125 nM 2 (e) b+1.25 uM 2 (f) b+12.5 uM 2.

Cell viability studies using live-cell penetrating Calcein AM as a fluorophore show that 2 is protective against BSO assault from 1.25 nM to 12.5 µM with an $EC_{50}$ 31.46±4.96 nM (FIG. 10). This dose response is visualized in the fluorescent cell images shown in FIG. 11 with increased cell survival corresponding to increasing 2 in the nM range. As has been mentioned with respect to 1 above, an interesting feature to be noted from these cellular studies is the fact that both 1 and 2 are capable of entering cells and do not appear to interrupt the vital functions of cytosolic metalloenzymes via extraction metal ions from those functionalities. This permeability and biocompatibility is a characteristic that can be exploited in future studies.

Beta-Amyloid Prevention/Disaggregation.

Figure 12:
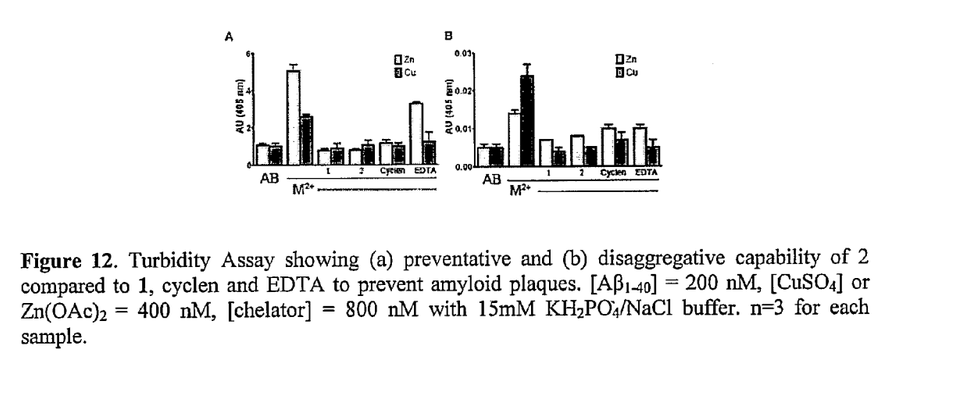
FIG. 12. are Turbidity Assays showing (a) preventative and (b) disaggregative capability of 2 compared to 1, cyclen and EDTA to prevent amyloid plaques.
Figure 13:
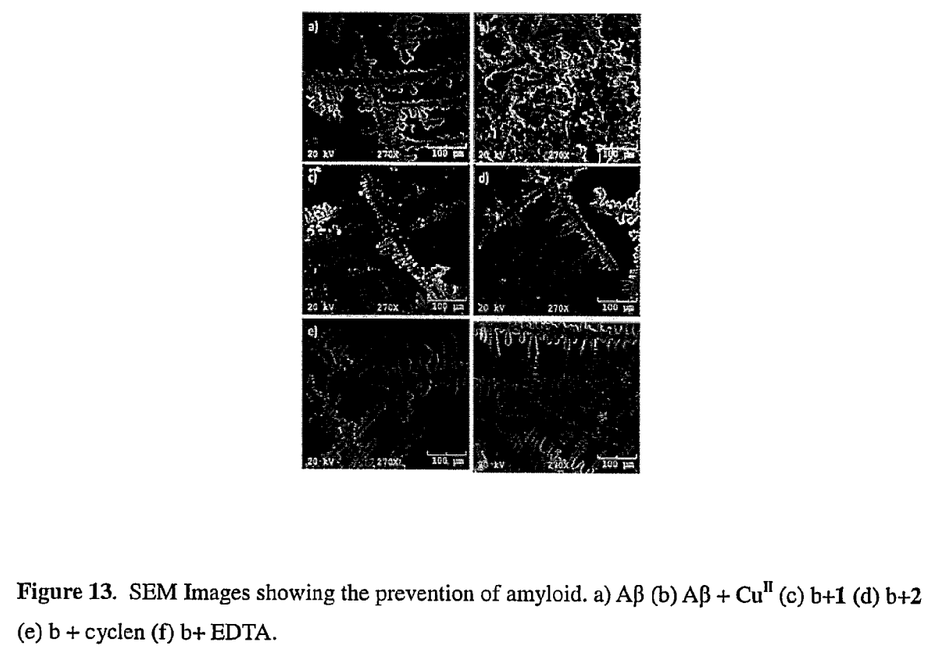
FIG. 13. is a series of SEM Images showing the prevention of amyloid. a) Aβ (b) Aβ+$Cu^{II}$ (c) b+1 (d) b+2 (e) b+cyclen (f) b+EDTA.

The macrocyclic compound 2 is also a chelator capable of preventing metal-induced amyloid formation as well as disaggregation. Metal ions bind to a histidine rich domain in amyloid producing Aβ in the form of insoluble plaques. This process has been extensively studied and described in a number of recent reviews. As shown in FIG. 12, copper (II) or zinc (II) ion addition to a solution of amyloid$_{1-40}$ results in a turbid solution which scatters light with a consequential increased absorbance signal using absorption spectrophotometry. Turbidity results shown in FIG. 12a show that incubation of 1 or 2 with Aβ$_{1-40}$ prior to addition of $Cu^{II}$ or $Zn^{II}$ prevents formation of aggregations compared to amyloid incubated with metal-ions alone. Moreover, amyloid aggregates formed by metal ion co-incubation can be disaggregated by the addition of 1 or 2 (FIG. 12b). These results were supported using the inherent fluorescence of Tyr[10] in the Aβ$_{1-40}$ sequence which is quenched upon aggregate formation. Chelators 1 and 2 are equally effective in preventing and re-constituting this signal. These results are compared to macrocyclic and open-chain chelators cyclen and EDTA, and show an equivalent preventative and disaggregative ability with respect to the formation of amyloid plaques.

An invention has been provided with several advantages. The interaction of redox active metal ions with amyloid is known to produce ROS that lead to neurological degradation associated with Alzheimer's disease. A molecular system capable of bimodal modulation of the metal-ions in amyloid as well as regulation of ROS would prove useful in combating this disease. To address these issues, Applicant's have shown that 1, a backbone commonly investigated for contrast agent imaging, may be repurposed as an anti-oxidant chelator for disaggregating amyloid. The antioxidant capacity was enhanced dramatically via conversion of the pyridine backbone to a pyridol to produce 2 with cellular studies showing superior antioxidant capacity while retaining chelation ability to protect amyloid from metal ions aggregation and also disaggregate amyloid aggregates. Direct reactions with $H_2O_2$ show that the pyridol backbone is the key to this ability due to the formation of di-keto species of 2.

While the invention has been shown in only one of its forms, it is not thus limited, but is susceptible to various changes and modifications without departing from the spirit thereof.

What is claimed is:

1. A molecule having the structural formula: